United States Patent
Long et al.

[11] Patent Number: 5,925,041
[45] Date of Patent: Jul. 20, 1999

[54] MONOPOLAR ELECTROSURGICAL TROCAR

[75] Inventors: Gary L. Long, Cincinnati; Lynetta J. Freeman, West Chester; Bryan D. Knodel, Cincinnati, all of Ohio

[73] Assignee: Ethicon Endo-Surgery, Inc., Cincinnati, Ohio

[21] Appl. No.: 08/878,421

[22] Filed: Jun. 18, 1997

Related U.S. Application Data

[63] Continuation-in-part of application No. 08/856,534, May 14, 1997.

[51] Int. Cl.[6] ................................................. A61B 17/39
[52] U.S. Cl. ............................. 606/41; 607/98; 606/45; 606/52
[58] Field of Search .................................. 606/41, 45–52

[56] References Cited

U.S. PATENT DOCUMENTS

| | | |
|---|---|---|
| 1,620,929 | 3/1927 | Wallerich . |
| 4,535,773 | 8/1985 | Yoon . |
| 4,674,010 | 6/1987 | van den Steen . |
| 4,717,438 | 1/1988 | Benge et al. . |
| 4,799,480 | 1/1989 | Abraham et al. . |
| 4,825,217 | 4/1989 | Choi . |
| 4,884,982 | 12/1989 | Fleming et al. . |
| 4,934,960 | 6/1990 | Capp et al. . |
| 4,936,842 | 6/1990 | D'Amelio et al. . |
| 5,105,829 | 4/1992 | Fabian et al. . |
| 5,124,509 | 6/1992 | Hoendervoogt et al. . |
| 5,207,691 | 5/1993 | Nardella . |
| 5,273,524 | 12/1993 | Fox et al. . |
| 5,342,356 | 8/1994 | Ellman et al. . |
| 5,344,420 | 9/1994 | Hilal et al. . |
| 5,354,191 | 10/1994 | Bales et al. ............................. 604/35 |
| 5,354,291 | 10/1994 | Bales et al. ............................. 604/35 |
| 5,380,321 | 1/1995 | Yoon . |
| 5,383,860 | 1/1995 | Lau . |
| 5,387,196 | 2/1995 | Green et al. . |
| 5,387,197 | 2/1995 | Smith et al. . |
| 5,391,166 | 2/1995 | Eggers . |
| 5,403,312 | 4/1995 | Yates et al. . |
| 5,417,687 | 5/1995 | Nardella et al. . |
| 5,432,486 | 7/1995 | Wong . |
| 5,437,277 | 8/1995 | Dumoulin et al. . |
| 5,443,462 | 8/1995 | Hannant . |
| 5,445,142 | 8/1995 | Hassler, Jr. . |
| 5,540,684 | 7/1996 | Hassler, Jr. . |
| 5,545,142 | 8/1996 | Stephens et al. . |
| 5,562,611 | 10/1996 | Transue . |
| 5,591,192 | 1/1997 | Privitera et al. . |
| 5,597,107 | 1/1997 | Knodel et al. . |
| 5,599,348 | 2/1997 | Gentelia et al. ............................. 606/45 |
| 5,658,279 | 8/1997 | Nardella et al. ............................. 606/45 |
| 5,733,323 | 3/1998 | Buck et al. ............................. 607/122 |

FOREIGN PATENT DOCUMENTS

WO 95/20921  2/1994  WIPO .

*Primary Examiner*—Michael Peffley
*Assistant Examiner*—Roy Gibson
*Attorney, Agent, or Firm*—Bernard E. Shay

[57] ABSTRACT

In the present invention, a surgical trocar is adapted to conduct monopolar electrosurgical energy to specially adapted cordless monopolar electrosurgical instruments. In one embodiment of the present invention, an electrosurgical trocar includes a cannula, an electrosurgical adapter and a locking connector adapted to connect the cannula to the electrosurgical adapter.

11 Claims, 5 Drawing Sheets

MONOPOLAR ELECTROSURGICAL TROCAR

This is a continuation-in-part of application Ser. No. 08/856,534, filed May 14, 1997, which is hereby incorporated herein by reference.

FIELD OF THE INVENTION

The present invention relates, in general, to an improved electrosurgical trocar adapted to provide electrosurgical energy to specially adapted cordless electrosurgical instruments used with the electrosurgical trocar and, more particularly, to a monopolar electrosurgical trocar and trocar adapter.

BACKGROUND OF THE INVENTION

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. Once the puncture is made, the obturator is withdrawn from the cannula. The cannula then provides a small diameter passageway into and through the body wall to provide access for additional surgical instrumentation to the surgical site. The function, structure and operation of a typical trocar is described in detail in U.S. Pat. No. 5,387,197, which is hereby incorporated herein by reference.

Such additional surgical instruments may include, for example, bipolar or monopolar electrosurgical instruments which utilize radio frequency electrosurgical energy. Known electrosurgical instruments include, for example, bipolar forceps, bipolar scissors, monopolar-hook, monopolar-scissors and, bipolar endocutters. Each of those instruments has an electrosurgical end effector which is adapted to treat tissue through the application of electrosurgical (e.g. radio frequency or RF) energy to tissue which is brought in contact with the electrosurgical end effector. Most known electrosurgical instruments are connected by electrical cords to electrosurgical generators. The structure and operation of a typical bipolar cutter/stapler ("bipolar endocutter") is described in U.S. Pat. No. 5,403,312 which is hereby incorporated herein by reference. The structure and operation of typical monopolar electrosurgical instruments is described in U.S. Pat. No. 5,207,691 and U.S. Pat. No. 5,273,524 which are hereby incorporated herein by reference.

Electrosurgical generators, such as the Force II generator which is available from Valley Lab of Bolder Colo., supply electrical energy to the electrosurgical instruments through electrical cords. The electrical cords, being attached directly to the electrosurgical instrument, may make the electrosurgical instrument inconvenient to use. Alternatively, electrical cords may cause undesirable delays as one electrosurgical instrument is unplugged from the generator and another is plugged in. Thus, it would be advantageous to design a cordless electrosurgical instrument. However, such a cordless electrosurgical instrument would have to be connected to the electrosurgical generator through some alternate arrangement. Therefore, it would also be advantageous to design a trocar or a trocar adapter which is adapted to conduct electrosurgical energy to specially designed cordless electrosurgical instruments. In particular, it would be advantageous to design a monopolar electrosurgical trocar or trocar adapter particularly adapted for use with monopolar electrosurgical instruments.

SUMMARY OF THE INVENTION

In the present invention, a monopolar surgical trocar or trocar adapter is adapted to conduct electrosurgical energy to specially adapted cordless electrosurgical instruments. In one embodiment of the present invention, an electrosurgical trocar includes a cannula, an electrosurgical adapter and a locking connector adapted to connect the cannula to the electrosurgical adapter. The cannula is an elongated tube which may be inserted into a body cavity, duct or vessel. The electrosurgical adapter includes a housing with an elongated central aperture, at least one electrical contact positioned in and extending axially along the elongated aperture, at least one internal electrical conductor, at least one external conductor, an outer housing and an electrical cord. An electrosurgical trocar or trocar adapter according to the present invention may also include a compression mechanism.

In a further embodiment of the present invention, the adapter aperture is formed by an aperture wall positioned in the adapter housing. The electrical contact is positioned in and extends axially along the aperture, forming at least a portion of the walls of the aperture. The electrical contact may be divided into two pieces within the aperture. The internal electrical conductor connects the electrical contact to the external connector. The compression mechanism biases the pieces of the electrical contact toward the center of the adapter aperture. An electrical cord is connected to the external connector such that the electrical cord may be used to plug the adapter into one output of an electrosurgical generator. A return electrode may be affixed to the skin of the patient as in a conventional monopolar arrangement.

In a further embodiment of the present invention, the electrical contact is divided into a first stator plate and a second stator plate. The second stator plate is positioned opposite the first stator plate. The second stator plate is electrically connected to the first stator plate. The compression member includes one or more compression rings positioned around the first and second electrical contacts.

In a further embodiment of the present invention, the electrosurgical trocar includes a locking connector which connects the cannula to the adapter. In this embodiment of the invention, the adapter includes first and second locking cleats extending from the distal end of the connector. The cannula includes receptors such as indentations or ribs which hold the distal ends of the locking cleats in place, thus holding the connector in contact with the cannula.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
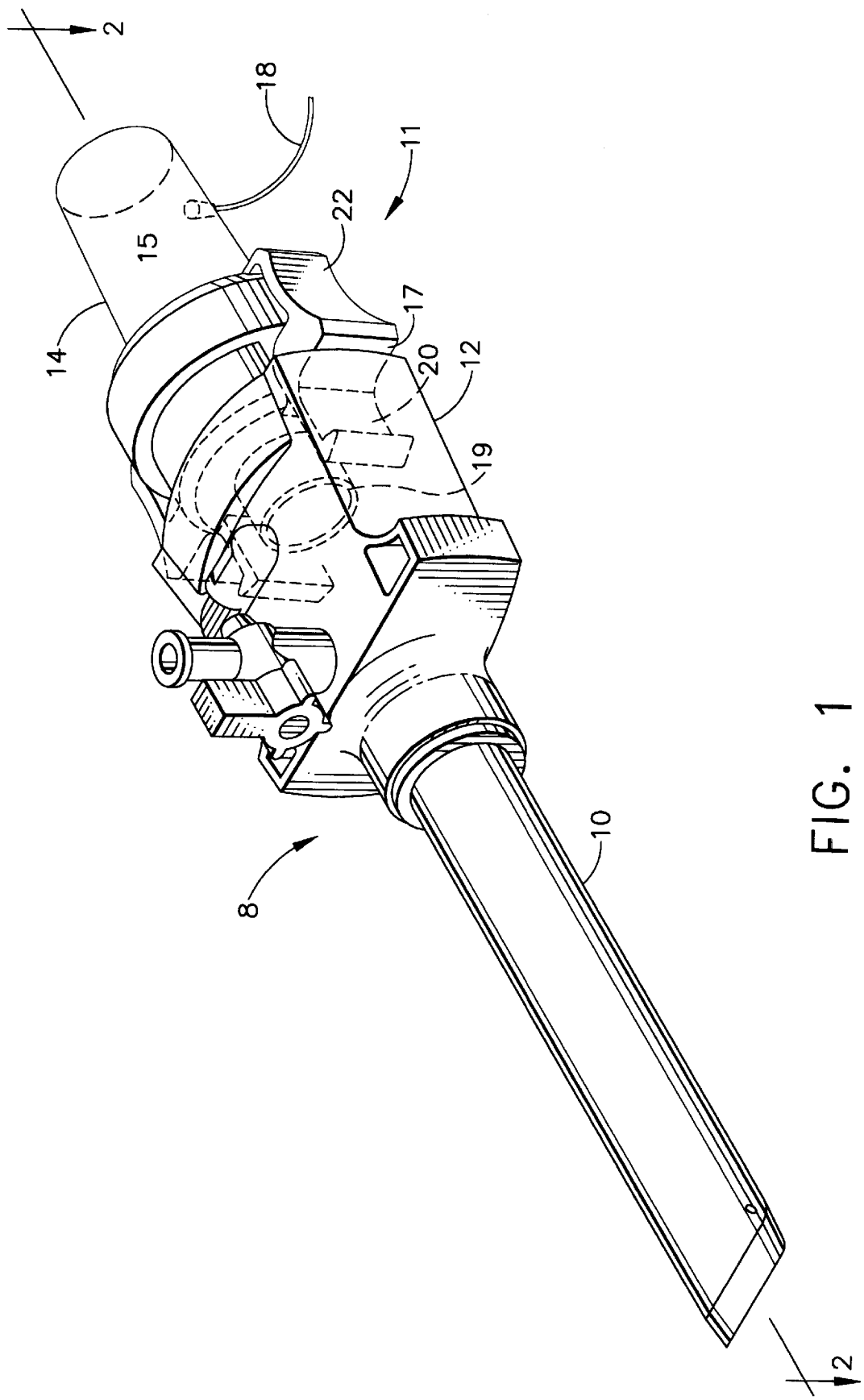
FIG. 1 is a perspective view of a monopolar electrosurgical trocar according to the present invention.

FIG. 1 is a perspective view of a monopolar electrosurgical trocar according to the present invention. Electrosurgical trocar 11 includes trocar cannula 8 and electrosurgical adapter 14. Electrosurgical trocar 11 may also include an obturator assembly (not shown) such as the one illustrated in U.S. Pat. No. 5,387,197, which has been previously incorporated herein by reference. Trocar cannula 8 includes cannula housing 12 and cannula tube 10, extending from housing 12. Electrosurgical adapter 14 includes an adapter housing 15, locking connector 17 and an electric cord 18. In the embodiment of the invention illustrated in FIG. 1, electrosurgical adapter 14 is connected to trocar cannula 8 by locking connector 17. Locking connector 17 includes locking cleat 20 and release button 22. It will be apparent that electrosurgical adapter 14 may be integrated directly into trocar cannula 8, thus eliminating the need for locking connector 17.

Figure 2:
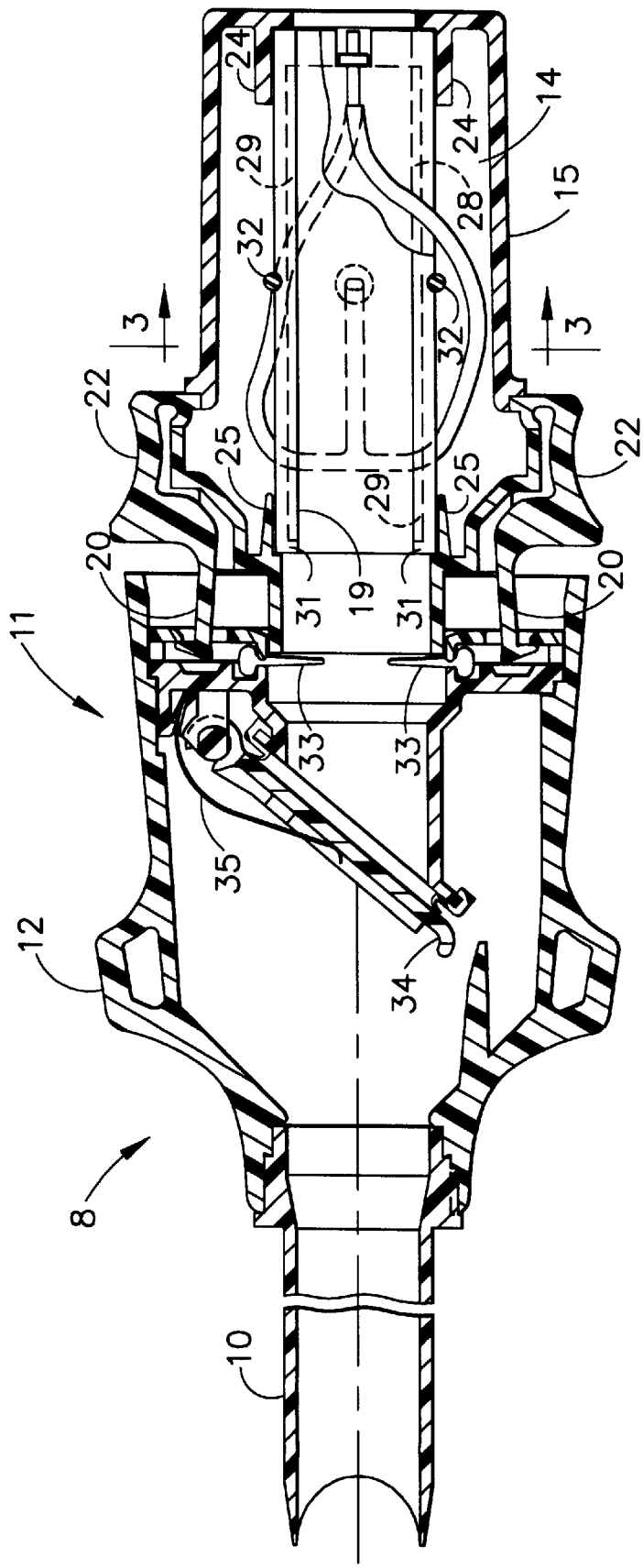
FIG. 2 is a plan view section taken through the electrosurgical trocar illustrated in FIG. 1.

FIG. 2 is a plain view section taken through electrosurgical trocar 11. In FIG. 2, cannula housing 12 includes flapper valve 34 and ring gasket 33. Electrosurgical adapter 14 includes central aperture 19, front flange 25 and base flange 24. Aperture 19 is an elongated aperture for receiving working instruments such as endoscopic electrosurgical instruments. Electrosurgical adapter 14 further includes one or more interior electrical contacts which, in the embodiment illustrated in FIGS. 2 and 3, comprise stator plates 28 and 29. At least a portion of the interior wall of central aperture 19 is formed by upper insulator 30 and upper stator plate 28. Upper insulator 30 is positioned against front flange 25 and base flange 24. Compression member 32 is, in the present embodiment, an o-ring which is positioned outside of upper insulator 30 to bias upper insulator 30 and upper stator plate 28 toward the center of central aperture 19. Compression member 32 may also be, for example, a spring, a flexible sleeve, a plurality of o-rings or any other suitable biasing member.

Figure 3:
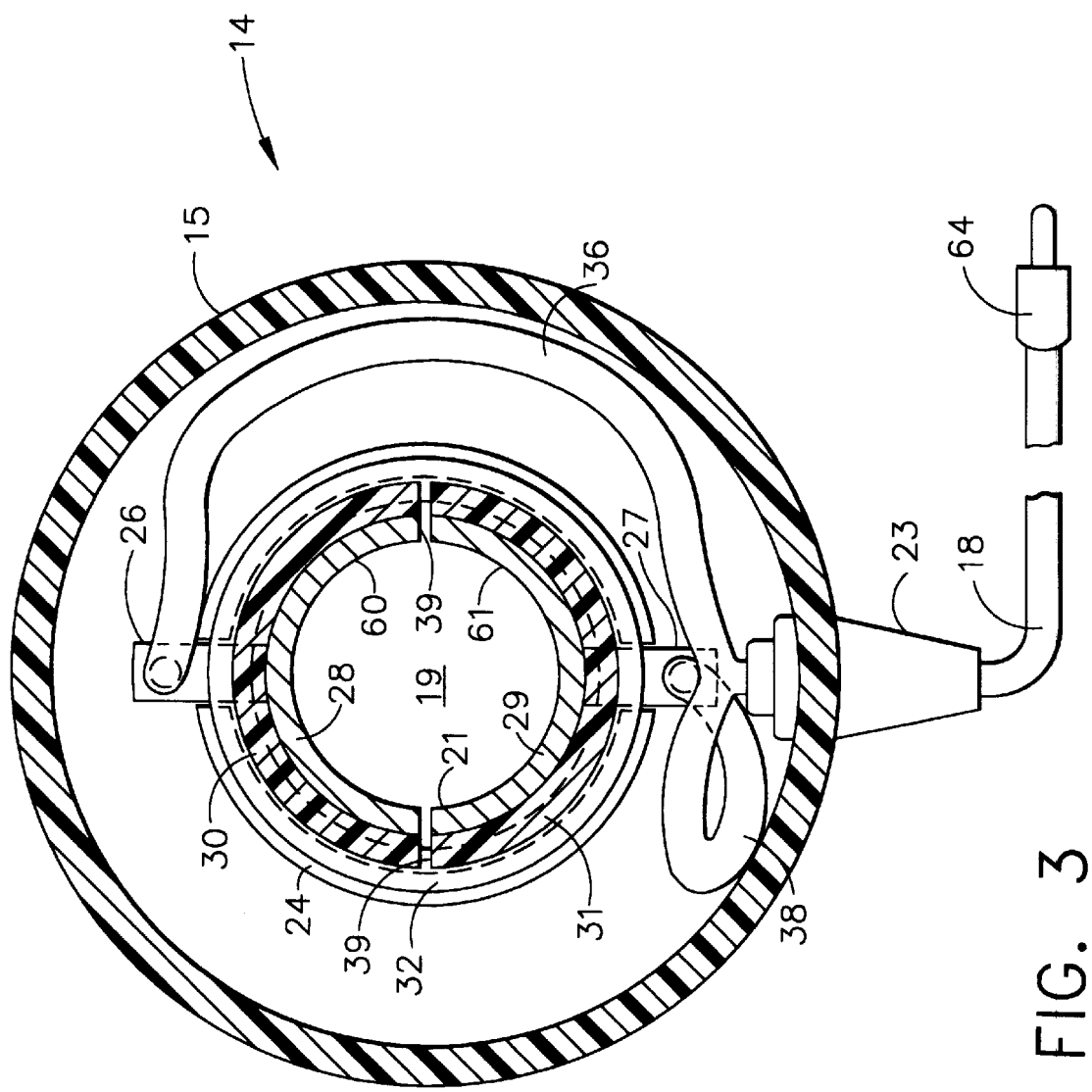
FIG. 3 is a section view taken along line 3—3 of FIG. 2.

FIG. 3 is a sectional view of electrosurgical adapter 14 taken along line 3—3 of FIG. 2. Central aperture 19 is defined by aperture interior wall 21. The portion of interior wall 21 visible in FIG. 3 is formed, at least in part, by upper contact surface 60 of upper stator plate 28 and lower contact surface 61 of lower stator plate 29. Upper stator plate 28 and lower stator plate 29 are positioned on, and may be electrically insulated from one another by, upper insulator 30 and lower insulator 31, respectively. Alternatively, upper stator plate 28 and lower stator plate 29 may be in electrical contact. In a further alternative embodiment, stator plate 28 and stator plate 29 may be joined to form a single electrode, which single electrode may or may not include a compression gap 39. In order to ensure that contact is maintained, compression gap 39 must be relatively small and, in particular, compression gap 39 should be smaller than the diameter of the contact electrode on any electrosurgical instrument used with electrosurgical trocar 11. Compression member 32 surrounds upper insulator 30 and lower insulator 31. Compression member 32, which is an o-ring in the embodiment of FIGS. 2–3, biases upper insulator 30 and lower insulator 31 toward the center of central aperture 19. Electric cord 18 is connected to upper stator plate 28 by upper conductor 36 and upper stator tab 26. Electric cord 18 is connected to lower stator plate 29 by lower conductor 38 and lower stator tab 27. Upper conductor 36 may be electrically connected to lower conductor 38 such that upper stator plate 28 and lower stator plate 29 are electrically common. Base flange 24, which is part of adapter housing 15, holds upper insulator 30 and lower insulator 31 in place. Strain relief 23 protects electric cord 18 as it passes through adapter housing 15. Electric cord 18 may be plugged into a suitable electrosurgical generator using, for example, a monopolar plug 64.

Figure 4:
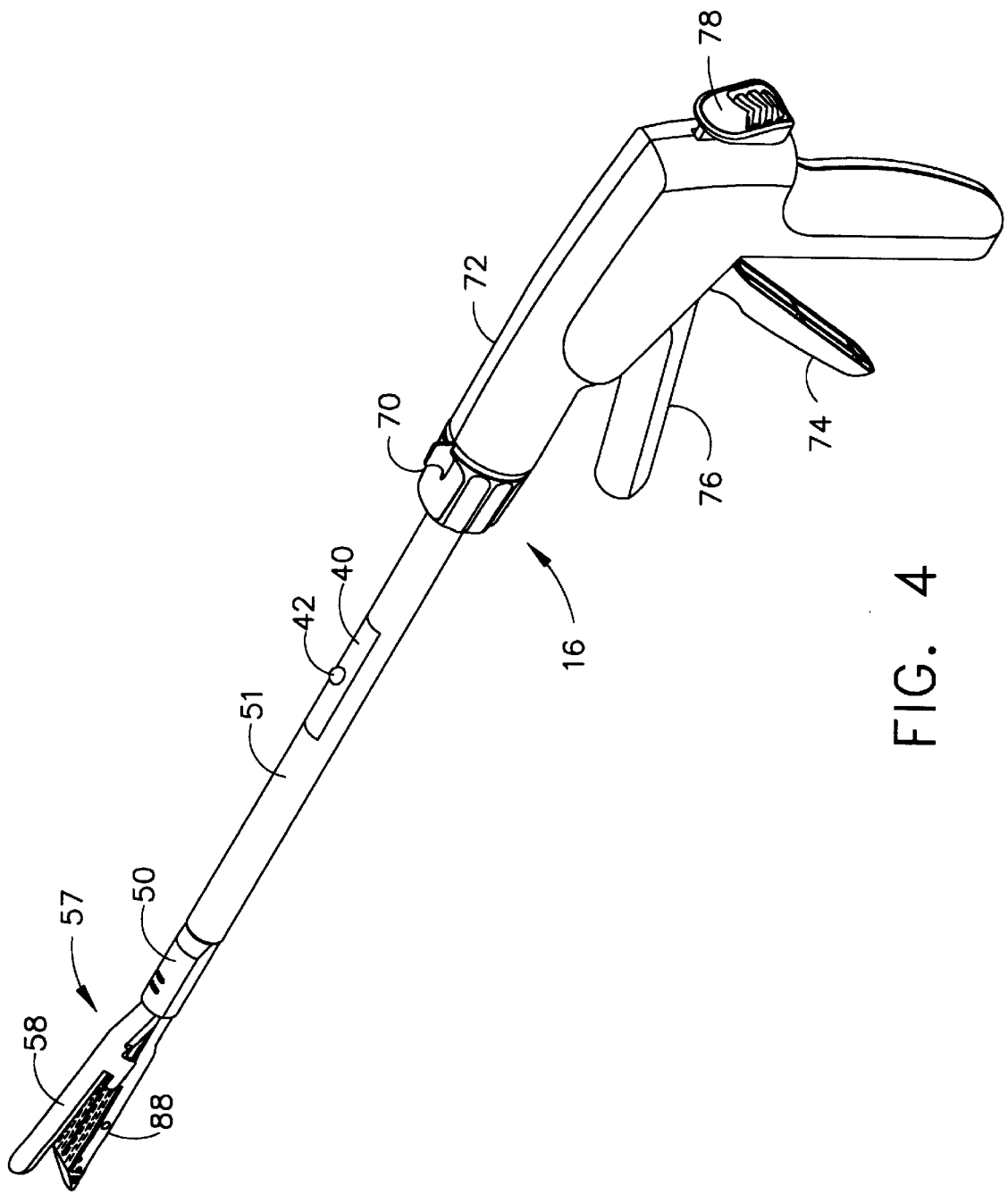
FIG. 4 is a perspective view of a cordless electrosurgical instrument according to the present invention.

FIG. 4 is a perspective view of a cordless monopolar electrosurgical instrument which may be, for example, a monopolar cutter/stapler. In FIG. 4, electrosurgical instrument 16 includes handle 72, closure tube 50 and end effector 57. Closure tube 50 is elongated to facilitate insertion of end effector 57 through a trocar cannula (such as cannula tube 10 of electrosurgical trocar 11), thus facilitating the use of electrosurgical instrument 16 in endoscopic or laparoscopic surgical procedures. Handle 72, which is located at the proximal end of instrument 16, includes grasping trigger 74, firing trigger 76 and release trigger 78. Closure tube 50, which connects handle 72 to end effector 57, includes rotation knob 70, first contact insulator 40, instrument electrode contact 42 and outer tube 51. End effector 57, which is located at the distal end of closure tube 50 includes anvil 58 and cartridge channel 88 and may further include staple cartridge 68. Electrosurgical instrument 16 is similar in structure and operation to the endoscopic electrocautery linear cutting and stapling instrument illustrated and described in U.S. Pat. No. 5,403,312, which has been previously incorporated herein by reference, except that electrosurgical instrument 16, as illustrated in FIG. 4, is adapted to work as a cordless monopolar instrument. In electrosurgical instrument 16, electrosurgical energy is supplied to the instrument through instrument electrode contact 42.

Figure 5:
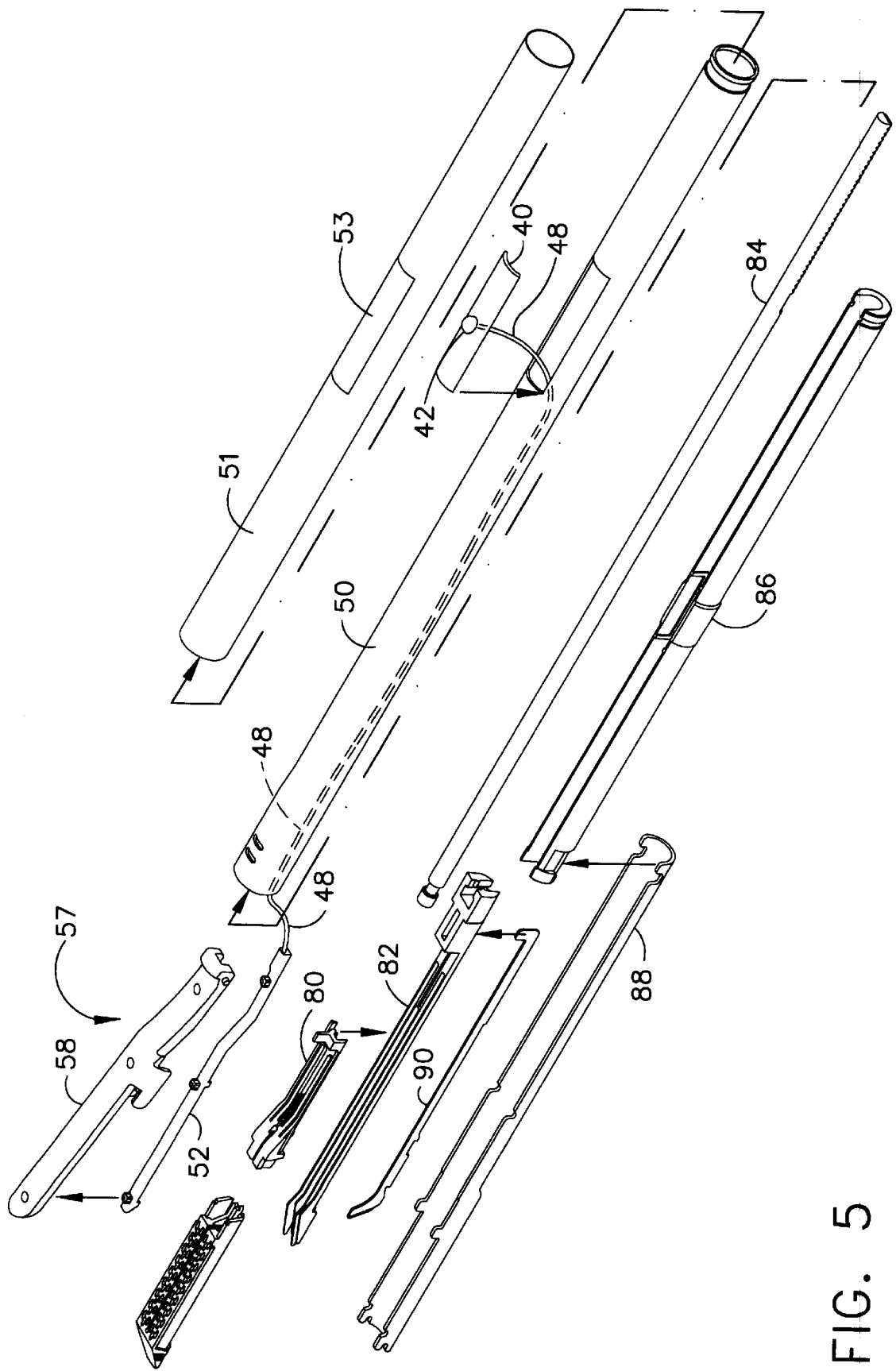
FIG. 5 is an exploded perspective view of the distal end of the cordless electrosurgical instrument illustrated in FIG. 4.

FIG. 5 is an exploded perspective view of the distal end of electrosurgical instrument 16. In FIG. 5, outer tube 51 is positioned over closure tube 50. In the instruments illustrated in FIGS. 4 and 5, closure tube 50 is electrically conductive and outer tube 51 is constructed of an electrically insulating material. Instrument electrode contact 42, which penetrates first contact insulator 40, extends through opening 53 in outer tube 51. First contact insulator 40 electrically isolates contact 42 from closure tube 50. In an alternate electrosurgical instrument, closure tube 50 may be constructed of an insulating material. Conductor 48 passes through closure tube 50 from electrode assembly 52 to instrument electrode contact 42, electrically connecting electrode assembly 52 to contact 42. Electrode assembly 52 is positioned in anvil 58. Electrode assembly 52 may be electrically insulated from anvil 58 and closure tube 50 to prevent electrode assembly 52 from shorting to anvil 58 or closure tube 50. Conductor 48 may be insulated to prevent it from shorting to closure tube 50 or any of the mechanisms in closure tube 50.

In the cordless electrosurgical instrument illustrated in FIGS. 4 and 5, knife 90 is connected to wedge assembly 82 and wedge assembly 82 is connected to firing rod 84, which, in turn, is operatively connected to firing trigger 76. Closure tube 50 is operatively connected to rotation knob 70, grasping trigger 74 and release trigger 78. Wedge guide 80 is fitted over wedge block assembly 82 to guide wedge block assembly 82 as firing rod 84 moves wedge block assembly 82. The structure and operation of the mechanical features of the device illustrated in FIGS. 4 and 5 may be better understood with reference to the mechanical cutting and stapling instrument illustrated and described in U.S. Pat. No. 5,597,107 which is hereby incorporated herein by reference.

In the device illustrated in FIGS. 4 and 5, electrode assembly 52 acts as a primary electrode and a secondary or return electrode (not shown) is affixed to the skin of the patient in, for example, the manner illustrated in U.S. Pat. No. 5,207,691 which has been previously incorporated herein by reference. When electrically conductive tissue is grasped by end effector 57 and an electrosurgical generator is connected to first instrument electrode contact 42 and a second electrode is connected to the patient's skin, electrosurgical energy will flow through the grasped tissue to the external electrode, coagulating the grasped tissue.

In operation, trocar cannula 8 is used with a conventional trocar orbitor (not shown) to penetrate the wall of a body cavity such as, for example, the abdominal wall of a human being. After the body wall is penetrated, the obturator assembly is withdrawn from trocar cannula 8, and the cannula is used as an access portal for the passage of various endoscopic instruments to provide access to internal organs. Where the endoscopic instrument to be used is a monopolar cordless electrosurgical instrument such as electrosurgical instrument 16, electrosurgical adapter 14 may be attached to trocar cannula 8. Once electrosurgical adapter 14 is attached to trocar cannula 8 and electric cord 18 is attached to a suitable electrosurgical generator (not shown), electrosurgical trocar 11 may be used to provide electrosurgical energy to cordless electrosurgical instruments such as monopolar electrosurgical instrument 16.

When a cordless electrosurgical instrument such as monopolar electrosurgical instrument 16 is inserted into a body cavity through electrosurgical trocar 11, end effector 57 passes through trocar cannula 8 and into the body cavity while most of closure tube 50 remains in the trocar. Handle 72, which is outside of trocar 11, is manipulated by the surgeon to control the position of end effector 57.

Electrosurgical energy is provided to instrument 16 by the interaction of contact 42 with the stator plates 28 and 29. The diameter of central aperture 19 generally corresponds with the outer diameter of closure tube 50, including outer tube 51, so that closure tube 50 slides through central aperture 19 and the interior of cannula tube 10. Contact 42, being raised above the surface of closure tube 50 and outer tube 51, will scrape against stator plates 28 and 29 as closure tube 50 passes through aperture 19. Compression member 32 will ensure that stator plates 28 and 29 maintain electrical contact with contact 42, maintaining a good electrical connection between the stator plates in adapter 14 and the contact point on instrument 16. Electrical contact will be maintained so long as contact 42 is positioned in central aperture 19 opposite at least one of stator plates 28 and 29. Electrical contact may be enhanced by using multiple contact points on instrument 16.

With contact 42 in contact with one of stator plates 28 and 29, electrosurgical energy may be supplied to electrosurgical trocar 11 through electric cord 18. The electrosurgical energy passes through conductors 36 and 38, stator tabs 26 and 27 and stator plates 28 and 29 into instrument 16 via contact 42. Electrosurgical energy supplied to instrument 16 via contact 42 may be supplied to end effector 57 via the circuit formed by first instrument electrode contact 42, conductor 48, and electrode assembly 52. This circuit is completed when tissue or other conductive material is grasped by end effector 57, providing a path from electrode assembly 52 to the grasped or touched tissue and through the patient to an external pad electrode. One or more switches may be included at any point in this circuit to control the flow of electricity to end effectors 57.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical adapter wherein the electrosurgical adapter comprises:
   a) an aperture wall surrounding an elongated central aperture extending from a first end of said adapter to a second end of said adapter;
   b) a first electrical contact positioned in and extending axially along said elongated aperture wherein said first electrical contact comprises:
      i) a first stator plate, wherein said first stator plate comprises a first portion of said aperture wall;
      ii) a second stator plate electrically connected to said first stator plate, wherein said second stator plate comprises a second portion of said aperture wall;
   c) a first electrical conductor connecting said first electrical contact to a first external connector,
   d) an outer housing surrounding said aperture and said first electrical contact; and
   e) an electrical cord connected to said first external connector and extending from said outer housing.

2. An electrosurgical adapter according to claim 1 wherein said adapter further comprises a compression mechanism adapted to bias said electrical contact toward the center of said aperture and said compression mechanism comprises a compression member surrounding said stator plates.

3. An electrosurgical adapter according to claim 2 wherein said compression member comprises one or more compression rings.

4. An electrosurgical adapter wherein the electrosurgical adapter comprises:
   a) an aperture wall surrounding an elongated central aperture extending from a first end of said adapter to a second end of said adapter;
   b) a first electrical contact positioned in and extending axially along said elongated aperture, wherein said first electrical contact comprises:
      i) a first stator plate, wherein said first stator plate comprises a first portion of said aperture wall;
      ii) a second stator plate electrically connected to said first stator plate, wherein said second stator plate comprises a second portion of said aperture wall;
   c) a first electrical conductor connecting said first electrical contact to a first external connector;
   d) a compression mechanism wherein said compression mechanism is adapted to bias said first and second stator plates toward the center of said aperture, said compression mechanism comprising a compression member surrounding said stator plates, wherein said compression member comprises one or more compression rings;
   e) an outer housing surrounding said aperture and said first electrical contact; and
   f) an electrical cord connected to said first external connector and extending from said outer housing.

5. An electrosurgical trocar, including a trocar adapter, wherein said adapter comprises:
   a) an aperture wall surrounding an elongated central aperture extending from a first end of said adapter to a second end of said adapter;

b) a first electrical contact positioned in and extending axially along said elongated aperture wherein said first electrical contact comprises:
   i) a first stator plate, wherein said first stator plate comprises a first portion of said aperture wall; and
   ii) a second stator plate electrically connected to said first stator plate, wherein said second stator plate comprises a second portion of said aperture wall;
e) a first electrical conductor connecting said first electrical contact to a first external connector;
f) an outer housing surrounding said aperture and said first electrical contact; and
g) an electrical cord connected to said first external connector and extending from said outer housing.

6. An electrosurgical trocar according to claim 5, wherein said compression mechanism comprises a compression member surrounding said stator plates.

7. An electrosurgical trocar according to claim 6, wherein said compression member comprises one or more compression rings.

8. An electrosurgical adapter wherein the electrosurgical adapter comprises:
   a) an aperature wall surrounding an elongated central aperture including a central axis extending from a first end of said adapter to a second end of said adapter;
   b) first electrical contact means for providing electrical energy to instruments placed in said aperture, said first contact means being positioned in and extend axially along said elongated aperture wherein said first electrical contact means are electrically connected;
   c) a first electrical conductor connecting said first electrical contact means to a first external connector means for connecting said first electrical conductor to an external source of electrical energy;
   d) an outer housing surrounding said aperture and said first electrical contact means; and
   e) an electrical cord connected to said first external connector means and extending from said outer housing.

9. An electrosurgical adapter according to claim 8, wherein said first and second electrical contact means comprise:
   a) a first stator plate, wherein said first stator plate comprises a first portion of said aperture wall; and
   b) a second stator plate electrically connected to said first stator plate, wherein said second stator plate comprises a second portion of said aperture wall.

10. An electrosurgical adapter according to claim 8 wherein said adapter further comprises a compression means adapted to bias said first electrical contact means towards said central axis of said aperture.

11. An electrosurgical adapter according to claim 10 wherein said compression member comprises one or more compression ring means for providing substantially equal pressure around said aperture.

* * * * *